United States Patent [19]

Igaue et al.

[11] Patent Number: 5,522,811
[45] Date of Patent: *Jun. 4, 1996

[54] TOPSHEET FOR USE IN DISPOSABLE BODY FLUID ABSORPTIVE GOODS

[75] Inventors: Takamitsu Igaue; Tsutomu Kido; Hisashi Takai, all of Kawanoe, Japan

[73] Assignees: Uni-Charm Corporation, Ehime-ken; Mitsui Petrochemical Industries, Ltd., Tokyo, both of Japan

[*] Notice: The term of this patent shall not extend beyond the expiration date of Pat. No. 5,449,352.

[21] Appl. No.: 154,117

[22] Filed: Nov. 18, 1993

Related U.S. Application Data

[63] Continuation-in-part of Ser. No. 114,839, Sep. 2, 1993, Pat. No. 5,383,870.

[30] Foreign Application Priority Data

Nov. 30, 1992 [JP] Japan .................................. 4-320619

[51] Int. Cl.$^6$ .............................. A61F 13/15; A61F 13/20
[52] U.S. Cl. ...................... 604/378; 604/366; 604/370; 604/383; 604/385.1
[58] Field of Search .......................... 604/358, 366–367, 604/370, 375, 378–385.1; 602/43–47

[56] References Cited

U.S. PATENT DOCUMENTS

| | | |
|---|---|---|
| 4,184,902 | 1/1980 | Karami . |
| 4,397,644 | 8/1983 | Matthews et al. ...................... 604/370 |
| 4,634,440 | 1/1987 | Widlund et al. ...................... 604/385.1 |
| 4,655,877 | 4/1987 | Horimoto et al. . |
| 4,726,976 | 2/1988 | Karami . |
| 4,828,555 | 5/1989 | Hermansson ............................. 604/329 |
| 5,383,870 | 1/1995 | Takai et al. ............................. 604/358 |

FOREIGN PATENT DOCUMENTS

| | | |
|---|---|---|
| 57-17081 | 4/1982 | Japan . |
| 60-259261 | 12/1985 | Japan . |
| 4-152945 | 5/1992 | Japan . |
| 4152945 | 5/1992 | Japan ..................................... 604/366 |
| 2180271 | 3/1987 | United Kingdom . |
| 0545423 | 6/1993 | United Kingdom . |

Primary Examiner—Randall L. Green
Assistant Examiner—P. Zuttarelli
Attorney, Agent, or Firm—Lowe, Price, LeBlanc & Becker

[57] ABSTRACT

A topsheet for use in body fluid absorptive goods includes an upper sheet having a skin-contacting area and a plurality of liquid passages each having upper and lower openings. A lower sheet underlies the upper sheet. The lower sheet is welded to the upper sheet around the lower openings and extends into each of the liquid passages along a limited extent thereof.

8 Claims, 2 Drawing Sheets

TOPSHEET FOR USE IN DISPOSABLE BODY FLUID ABSORPTIVE GOODS

RELATED APPLICATIONS

The present application is a continuation-in-part of prior application Ser. No. 114,839, filed Sep. 2, 1993, entitled "Liquid-Permeable Topsheet for Body Fluid Absorptive Goods," now U.S. Pat. No. 5,383,870.

BACKGROUND OF THE INVENTION

The present invention relates to liquid-permeable topsheets for use in disposable body fluid absorptive goods such as sanitary napkins, disposable diapers and training pants.

In liquid-permeable topsheets used for body fluid absorptive goods, a technique is well known to make the topsheet from plastic film or nonwoven fabric and provide some with liquid through passages extending from top to bottom thereof. An upper surface of the topsheet is adapted to contact the wearer's skin, and lower openings of the respective liquid passages contact an absorbent core so that capillary action occurring within each liquid passage may be utilized to transfer excreted body fluids toward the absorbent core.

For example, Japanese Patent Publication No. 1982-17081 discloses a technique according to which a topsheet made of polyethylene film is provided with conically tapered liquid passages and the lower ends of the respective passages are arranged so as to be closely in contact with an absorbent core.

According to a technique disclosed by Japanese patent application Disclosure Gazette No. 1985-259261, a topsheet made of plastic film is provided with cylindrical liquid passages with their lower ends extending into an absorbent core, on one side, and a fibrous layer is bonded to the lower surface of the topsheet with fibres thereof extending into the liquid passages, on the other side. Such cylindrical liquid passages are more stable and therefore less deformable than the conical liquid passages under the same large load. Additionally, the cylindrical liquid passages are preferred to the conical liquid passages in that the fibres extending into the liquid passages also contribute to accelerate body fluids to be transferred toward the absorbent core under the capillary action.

According to a technique disclosed by Japanese patent application Disclosure Gazette No. 1992-152945, there is provided a high density area or rib continuously surrounding lower openings of respective liquid passages. This technique certainly stabilizes the opening of each liquid passage against deformation as well as collapse and allows body fluids to be effectively transferred toward an absorbent core.

Soft touch is essential to a topsheet, and therefore such conventional topsheets as disclosed by the above-mentioned Patent Publication and Disclosure Gazettes are also made from thin and soft materials. However, a disadvantage of the conical liquid passages disclosed by said Japanese Patent Publication No. 1982-17081 as well as the cylindrical liquid passages as disclosed by Japanese patent application Disclosure Gazette No. 1985-259261, is that the lower openings, i.e., free ends of those liquid passages are liable to be deformed, so the liquid passages readily collapse, for example, under the body weight of a wearer and a body fluids are often prevented from being smoothly transferred toward the absorbent core. While stability of each liquid passage against a compressive force exerted axially on the liquid passage can be more or less improved, such a liquid passage is still ready collapsible under a force exerted transversely on it since it comprises soft material. While the technique disclosed by the above-mentioned Japanese patent application Disclosure Gazette No. 1992-152945 may theoretically alleviate the problem of collapse, both the thickness of the topsheet and diameter of the liquid passage are unfeasibly fine, so that it would not be easy to provide the previously mentioned high density area or rib continuously surrounding the lower openings of the respective liquid passages although this is one of the most important features of the disclosed technique.

In view of these problems, unsolved by the prior art, it is a principal object of the invention to provide a topsheet comprising a first sheet and a second sheet underlying said first sheet wherein said first sheet is provided with liquid passages and said second sheet is welded to said first sheet around the lower openings of the respective liquid passages so as to restrict possibly occurring deformation of the liquid passages and thereby to solve the problems encountered by the conventional topsheets.

SUMMARY OF THE INVENTION

The object set forth above is achieved, according to the invention, with a topsheet for use in body fluid absorptive goods, formed with a plurality of liquid passages each extending through the topsheet from an upper opening to a lower opening thereof and a skin-contacting area continuously formed around the upper openings of the respective liquid passages. The topsheet comprises a first sheet including thermoplastic film or nonwoven fabric of thermoplastic fibres welded to each other, the liquid passages and the skin-contacting area, and a second sheet underlying the first sheet and including nonwoven fabric of thermoplastic fibres welded to each other and to the first sheet around lower openings of the respective liquid passages, and individual fibres extending upward and loosened from the second sheet around the lower openings into the respective liquid passages along inner walls thereof so that the second sheet is spaced from the first sheet except around the lower openings and thereby cooperates with the first sheet to define cavities extending in the direction of the topsheet thickness.

Preferably, the second sheet is hydrophilic in comparison with the first sheet.

The topsheet is obtained, for example, by blowing melt fibres from an extruder against the underside of the first sheet provided with the liquid passages and thereby forming melt-blown nonwoven fabric so that said let-blown fibres can be welded to the first sheet around the lower openings of the respective liquid passages and contribute to protect these passages from being deformed in the proximity of their lower openings. The first sheet and the second sheet are continuous with each other around the upper and lower openings of the respective liquid passages, so the liquid passages are substantially stabilized against deformation and collapse under an axial force as well as a transverse force exerted thereon.

Liquid excretions flow into the liquid passages and reaches the respective lower openings, whereupon the liquid excretions are absorbed by the absorbent core at spots of the core being in contact with the respective lower openings, and then spreads over the second sheet for absorbtion by the absorbent core also over an area being in contact with the second sheet. However, the second sheet thus wetted as a result of this spreading has no significant wet touch to a wearer, since the second sheet is welded to the first sheet around the respective lower openings but well spaced from the first sheet in the remaining zone.

BRIEF DESCRIPTION OF THE DRAWINGS

The invention will be described by way of example in reference with the accompanying drawings, in which.

DESCRIPTION OF THE PREFERRED EMBODIMENTS

Figure 1:
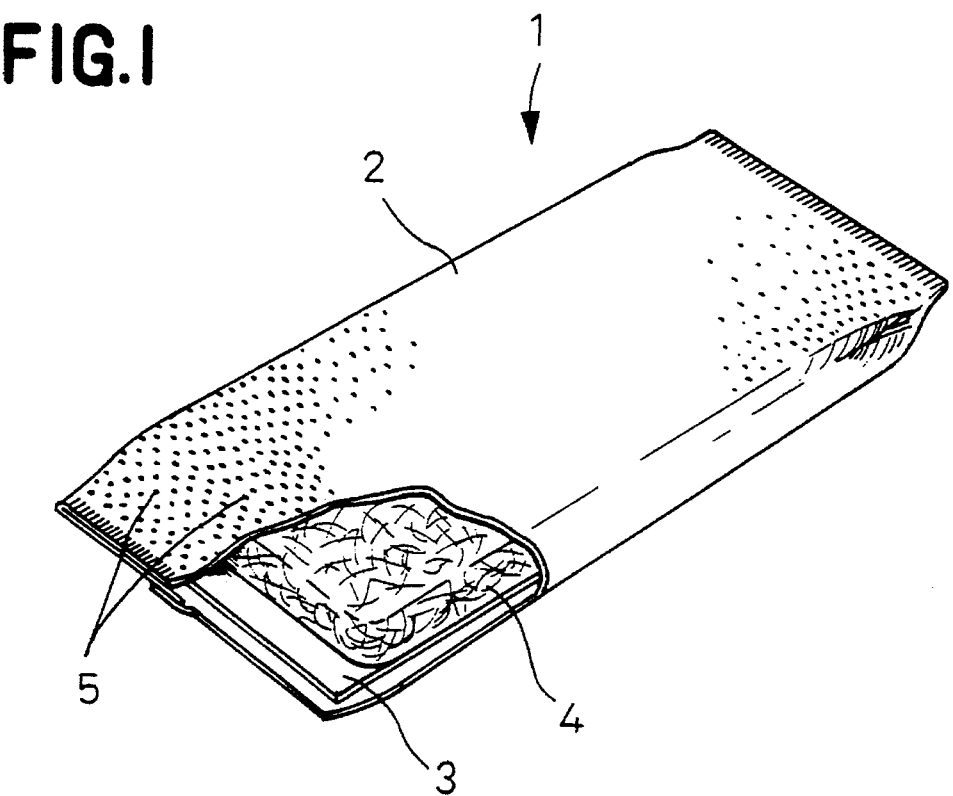
FIG. 1 is a perspective view showing, as partially broken away, a sanitary napkin.

Referring to FIG. 1, a sanitary napkin 1 comprises a liquid-permeable topsheet 2, a liquid-impermeable backsheet 3 and an absorbent core 4 sandwiched between these two sheets. The topsheet 2 entirely envelops the absorbent core 4 with the opposite side portions thereof being overlapped and sealed together on the backside of the napkin 1 and end portions extending along opposite ends of the absorbent core 4 being also sealed together. The backsheet 3 is interposed between the topsheet 2 lying on the backside of the napkin 1 and the absorbent core 4.

Figure 2:
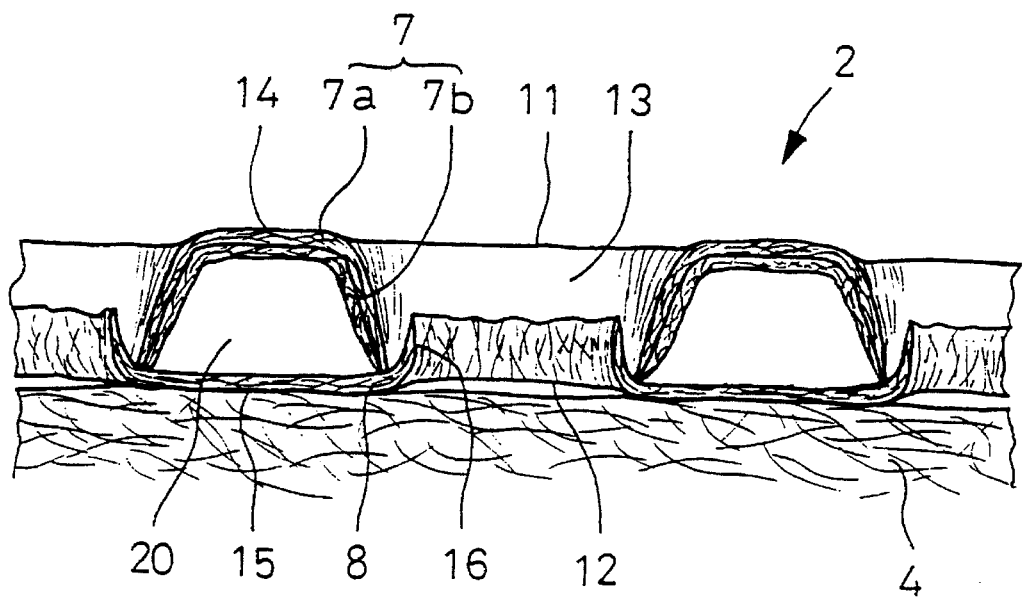
FIG. 2 is a sectional view partially showing a topsheet in an enlarged scale.

Referring to FIG. 2, the topsheet 2 is schematically illustrated in a partial section cut in the direction of its thickness. As illustrated, the absorbent core 4 contacts the underside of the topsheet 2. The topsheet 2 comprises an upper sheet 7 which comprises, in turn, a laminate of a first layer 7a and a second layer 7b both made of melt-blown fibres, and a lower sheet 8 underlying upper sheet 7 and made of melt-blown fibres. Upper sheet 7 includes a plurality of liquid passages 13 each extending through the sheet 7 from an upper opening 11 to a lower opening 12 and a skin-contacting area 14 which is formed as a continuous planar zone extending around the respective upper openings 11. The lower sheet 8 includes a planar area 15 which is formed as a continuous planar zone around the respective lower openings 12 and rising areas 16 extending from said planar area 15 upwardly into the respective liquid passages 13. The melt-blown fibres constituting the lower sheet 8 are welded to the upper sheet 7 around the respective lower openings 12 and thereby the lower sheet 8 is integrated with the upper sheet 7. However, these sheets 7, 8 define therebetween cavities 20, since the skin-contacting area 14 and the planar area 15 are spaced from each other.

Figure 3:
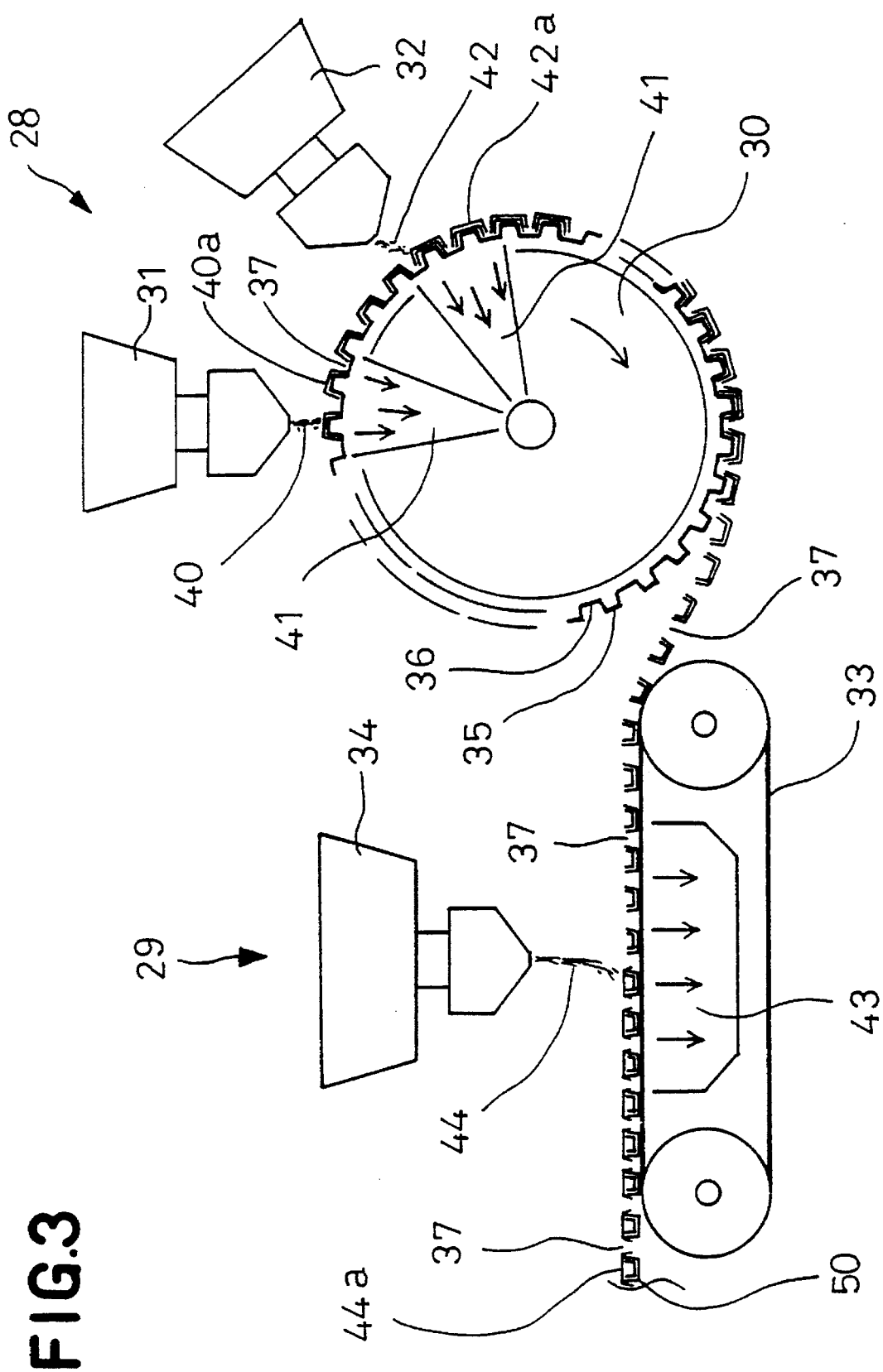
FIG. 3 is a schematic diagram illustrating a topsheet manufacturing process.

Referring to FIG. 3, a process of manufacturing the topsheet 2 is schematically illustrated. The process comprises a first forming step 28 utilizing a forming drum 30 and first and second melt-blowing extruders 31, 32 provided around said forming drum 30 and a second forming step 29 utilizing an endless belt 33 and a third melt-blowing extruder 34 provided above said endless belt 33. The forming drum 30 is provided around its outer peripheral surface with protrusions 35 and indents 36 which are alternately arranged and serve as forming dies so that melt-blown fibres 40 are blown from the first extruder 31 against said forming dies under effect of suction 41 to form a nonwoven fabric layer 40a destined to be the first layer 7a of the first sheet 7. Similarly, melt-blown fibres 42 are blown from the second extruder 32 against the nonwoven fabric layer 40a to form a nonwoven fabric layer 42a destined to be the second layer 7b of the first sheet 7. A laminate of these nonwoven fabric layers 40a, 42a is then formed by the drum 30 into a continuous first sheet 7 having the skin-contacting area 14 of the first sheet 7 formed by the protrusions 35 and the liquid passages 13 formed by the indents 36.

It should be understood that various factors such as respective amounts of the fibres 40, 42 to be blown, suction force 41 and depth of each indent 36 may be adjusted during the first forming step 28 to obtain a continuous first sheet 7 containing the fibres 40, 42 extending upward along side walls of the respective indents 36 so as to form the liquid passages 13 and openings formed by bottoms of the respective indents 36 destined to be the lower openings 12 of the first sheet 7.

The continuous first sheet 7 is separated from the peripheral surface of the forming drum 30 as it is transferred from the first forming step 28 to the second forming step 29, and laid on the endless belt 33 with its surface which has contacted the peripheral surface of the forming drum 30 facing upward. Under the effect of a suction 43, melt-blown fibres 44 are blown against said surface facing upward to form a nonwoven fabric layer 44a destined to be the second or lower sheet 8. The amount of the fibres 44a to be blown and intensity of the suction force 43 may be adjusted to assure that the fibres 44 are loosened around the openings 37 without formation of an apparent nonwoven fabric layer and extend upward into the liquid passages 13 along their inner walls without filling up the openings 37 destined to be the lower opening 12. The roll of sheet 50 comprising these nonwoven fabric layers 40a, 42a, 44a obtained in the manner as has been described above can be unrolled and cut into sheets of desired dimensions so as to be used as the individual topsheets 2.

In each topsheet 2 cut from the roll of sheet 50, the melt-blown fibres 40, 42 forming the first or upper sheet 7 are fluffed around the lower openings 12 in the direction of suction 41. The melt-blown fibres 44 blown from the third extruder 34 against this upper sheet 7 are welded and/or clung to the other melt-blown fibres 40, 42 and thereby integrate the second or lower sheet 8 with the upper sheet 7. By forming the upper sheet 7 in a two-layered structure comprising the melt-blown nonwoven fabric layers 40a, 42a as in the illustrated embodiment wherein the lower layer 40a of melt-blown nonwoven fabric having a higher density is first formed in order to make the topsheet 2 firm and then the upper layer 42a of melt-blown nonwoven fabric having a lower density is formed, goods utilizing such a topsheet 2 are provided which can give the wearer a cloth-like soft touch. It should be understood that the upper sheet 7 may be also formed by any one of the nonwoven fabric layers 40a, 42a.

The melt-blown fibres 40, 42, 44 may be of suitable thermoplastic resin such as polyethylene. It is also within the scope of the invention to replace the melt-blown nonwoven fabric of the upper sheet 7 by perforated plastic film. Preferably, the upper sheet 7 is made from suitable hydrophobic material so that a dry touch may be maintained even after excretion of body fluids, on one hand, and the lower sheet 8 is made hydrophilic in comparison with the upper sheet 7 so that the body fluids may be transferred toward the absorbent core and extensively spread over the lower sheet 8 as rapidly as possible, on the other hand. Such lower sheet 8 may be obtained, for example, by using polyethylene previously mixed with hydrophilic agent.

In the topsheet constructed according to the invention, the liquid passages are effectively shape-stabilized and difficult to be blocked, since the lower sheet is welded to the upper sheet around the lower openings of the respective liquid passages.

The body fluids excreted over the topsheet flow into the liquid passages and reach the lower openings of the respective liquid passages, whereupon the body fluids are absorbed by the portions of the absorbent core being in contact with these lower openings and simultaneously spread over the lower sheet, so the body fluids are absorbed also by the portion being in contact with said lower sheet. In this manner, the topsheet of the invention allows the absorption rate to be improved over the topsheet of prior art.

The lower sheet of the topsheet gives no wet touch to the wearer even after the lower sheet has been wetted with the body fluids spreading thereover, since there are the cavities defined between the upper sheet and the lower sheet.

An excellent shape-stability of the liquid passages improves a cushioning effect and therefore comfort of wearing the absorptive goods.

What is claimed is:

1. A topsheet for use in body fluid absorptive goods, comprising:
   (1) a first sheet including at least one of a thermoplastic film and nonwoven fabrics of thermoplastic fibers welded to each other,
   (2) a second sheet including a nonwoven fabric of thermoplastic fibers welded to each other,
   (3) said first sheet being formed with a plurality of liquid passages each having a sidewall and extending through said first sheet from an upper opening to a lower opening thereof and a skin-contacting area continuously formed around said upper openings, and
   (4) said second sheet underlying said first sheet, and
      a. being welded to said first sheet,
      b. being spaced from said first sheet except around said lower openings to thereby define cavities between said first and second sheets, and
      c. extending upward from adjacent said lower openings into substantially each of said liquid passages along said associated sidewall without filling up said liquid passages.

2. The topsheet according to claim 1, wherein said second sheet is hydrophilic in comparison with said first sheet.

3. The topsheet according to claim 1, wherein said first sheet comprises a perforated polyethylene film and said second sheet comprises a melt-blown nonwoven fabric of polyethylene.

4. The topsheet according to claim 1, wherein both said first sheet and said second sheet comprise a melt-blown nonwoven fabric of polyethylene, respectively.

5. The topsheet according to claim 1, wherein said second sheet comprises a melt-blown nonwoven fabric of polyethylene previously mixed with a hydrophilic agent.

6. The topsheet according to claim 1, wherein said first sheet comprises upper and lower layers of nonwoven fabrics, said upper layer having a density which is lower than that of said lower layer.

7. The top sheet according to claim 6, wherein both said upper and lower layers comprise melt-blown nonwoven fabrics.

8. The top sheet according to claim 1, wherein said second sheet avoids filling up said liquid passages by projecting upward into an associated one of said liquid passages from the lower opening thereof by a distance less than the length of said passage.

* * * * *